United States Patent [19]
Mapes et al.

[11] Patent Number: 5,030,561
[45] Date of Patent: Jul. 9, 1991

[54] CHLAMYDIA ASSAY USING AMIDINE MODIFIED SUPPORTS OR PARTICLES

[75] Inventors: James P. Mapes, Raleigh; Catherine S. Donahue, Cary, both of N.C.

[73] Assignee: Becton, Dickinson and Company, Franklin Lakes, N.J.

[21] Appl. No.: 289,888

[22] Filed: Dec. 27, 1988

[51] Int. Cl.$^5$ .......................................... G01N 33/571
[52] U.S. Cl. ................................. 435/7.36; 435/7.32; 435/14; 435/19; 435/21; 435/28; 436/510; 436/518; 436/534; 436/538; 436/541; 436/823
[58] Field of Search ............... 436/510, 511, 533, 538, 436/451, 808, 810, 823; 435/7, 20, 240.27, 7.36

[56] References Cited

U.S. PATENT DOCUMENTS

| | | | |
|---|---|---|---|
| 4,477,578 | 10/1984 | Miles et al. | 436/518 |
| 4,497,899 | 2/1985 | Armstrong et al. | 436/510 |
| 4,511,662 | 4/1985 | Baran et al. | 436/534 |
| 4,888,276 | 12/1989 | Shelburne | 435/240.27 |

OTHER PUBLICATIONS

Kricker, Ligand–Binder Assays, Chap. 3, Separation Procedures, Marcel Dekker, Inc. 1985, pp. 53–65.
Baker, et al., Immunoradiometric Assays, Chap. 5, Alternative Immunoassays, 1985, pp. 59–68.

*Primary Examiner*—Sam Rosen
*Attorney, Agent, or Firm*—Richard E. Brown

[57] ABSTRACT

A method for assaying of Chlamydia includes adhering Chlamydia antigen to amidine modified latex particles, binding of adhered antigen to an anti-Chlamydia antibody conjugated to an enzyme, separating the particles from the liquid phase of the assay and detecting bound enzyme by color development when the separated particles are contacted with a substrate for the enzyme. The invention includes a kit of materials for preforming an assay in accordance with the method of the invention.

22 Claims, No Drawings

CHLAMYDIA ASSAY USING AMIDINE MODIFIED SUPPORTS OR PARTICLES

BACKGROUND OF THE INVENTION

1. Field of the Invention

This invention relates to an assay for an analyte, and more specifically relates to an improved solid phase assay for Chlamydia.

2. Background of the Invention

The genus Chlamydiaceae includes two species, *Chlamydia trachomatis* and *Chlamydia psittaci*. *Chlamydia trachomatis* in its some fifteen various strains is the etiologic agent for a number of human ocular and genital diseases, including trachoma, inclusion conjunctivitis, lymphogranuloma venereum, "non-specific" or nongonococcal urethritis and proctitis. *C. trachomatis* infection is pervasive throughout the general population. It has been estimated, for instance, that *C. trachomatis* is accountable for several million cases per year of nongonococcal urethritis.

Since *C. trachomatis*-mediated disease is widespread, a reliable, simple and inexpensive test for the organism's presence is highly desirable and of great importance so that proper treatment can be undertaken. The only serological test in current use is the microimmunofluorescence test. This test, however, requires that the strains of *C. trachomatis* be used as serological test antigen. In addition, the facilities for conducting this test are available in only a limited number of laboratories throughout the world. The test is very laborious, time consuming and difficult to perform.

Several immunoassay procedures for Chlamydia have been disclosed. PCT-published application number WO 86/02733 discloses an assay for various antigens including Chlamydia which cause ocular infections. The assay includes immobilizing the antigen on a solid support by binding to a monoclonal antibody absorbed on the support, or the antigen is absorbed directly onto the solid support.

European Patent Application Number 0183383 discloses an assay for Chlamydia antigen which includes an isolation procedure in which the antigen is heated to a temperature of about 100° C. to reduce nonspecific binding.

Rose, in U.S. Pat. No. 4,663,291, discloses treating a specimen suspected of containing Chlamydia organisms with a surfactant and a metal ion to release Chlamydia antigen and assay of the antigen by known methods. In accordance with the method, the known inhibition of binding of the antigen to anti-Chlamydia antibody by the surfactant does not occur.

Armstrong et al. in U.S. Pat. No. 4,497,899, discloses an immunoassay for Chlamydia antigen in which a sample suspected of containing Chlamydia organisms is lysed to release the antigen which is absorbed directly onto a solid support.

In spite of the above disclosures, there yet remains a definite need for further improvement in assays for Chlamydia. It is toward fulfillment of this need that this invention is directed.

SUMMARY OF THE INVENTION

A method for determining Chlamydia organisms in a body sample includes adhering Chlamydia antigen to a solid support derivatized with amidine groups, binding adhered antigen to a tracer including an antibody bound to a label, separating the support having bound antigen from the liquid, and detecting bound tracer by a signal associated with the label. Preferably, the organisms are altered by treatment with a detergent reagent to achieve greater exposure of the antigen to the support. In the present disclosure, the term "determining" means qualitatively detecting the presence of Chlamydia organisms in the body sample or quantitatively determining the number of such organisms.

The preferred solid support is a polystyrene latex of amidine derivatized particles, and the preferred label is an enzyme conjugated to the antibody. A preferred method for separating is to filter the particles through a suitable membrane. The filtered particles are then preferably detected by contacting them on the membrane with a substrate which reacts with enzyme to give a color. A preferred enzyme substrate combination is alkaline phosphatase-indoxyl phosphate whereby the appearance of a blue color on the membrane indicates Chlamydia organisms in the body sample. The color may preferably be intensified by reacting the enzyme and substrate in the presence of, for example, a tetrazolium salt.

A kit of materials for performing the assay is included in the invention.

The amidine modified latex provides an assay which is greatly improved over a substantially identical assay using a latex containing particles which are not amidine modified. Because the antigen binds readily to the amidine groups, no trapping antibody is needed. In addition to greater sensitivity which is believed to be due to enhanced adherence of the antigen to the amidine groups, the assay is facile to perform, requiring only a few simple steps, and may be completed in a matter of 30 minutes or less.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

In accordance with the invention, the presence of Chlamydia organisms may be detected by assaying for an antigen using a particular solid support. It has been found that when Chlamydia antigen is incubated with a polymeric support modified with amidine groups, an assay of enhanced sensitivity is achieved as a result of significantly greater adherence of the antigen to the support relative to a conventional support.

Any polymeric support having pendant amidine groups may be used in the assay of the invention. Thus, for example, the support may be a styrene butadiene copolymer, a polyacrylate, or, preferably an amidine modified polystyrene. Amidine modified polymers may be prepared by polymerizing carboxy substituted olefinic monomers and converting the carboxylic acid or ester groups to amidine groups, or preferably, by converting acid or ester substituted olefinic monomers to the corresponding amidine substituted monomers and polymerizing. Conversion of carboxylic acids or esters to amidines is routine organic chemistry well known to those skilled in the art.

The solid support may be in any conventional form or shape such as sheets, plates, wells, beads, dipsticks, tubes and the like. Preferred solid supports are beads, most preferably latex particles. A particularly preferred solid support is an amidine modified polystyrene latex, available from Interfacial Dynamics, Portland, Oreg. The particles of the preferred latex may have a particle size of about 0.01 to 50 $\mu$, preferably about 0.1 to 10 most preferably about 0.4 to 1.0 $\mu$. The latex may be about 0.01 to 10, preferably about 0.1 to 4, most preferably about 1.0% solid on a weight per volume basis.

The amidine modified latex particles are incubated with Chlamydia antigen. The antigen may be obtained from a sample of a patient's body fluid suspected of containing Chlamydia organisms. A genital sample taken with a swab is generally preferred. The sample may be suspended in a liquid, such as a buffer, by agitating the swab in order to release the organisms into the buffer.

The assay may be performed with intact cells, however, it is preferred to pretreat the Chlamydia organisms to alter the cells to achieve greater exposure of the Chlamydia antigen. Any reagent which alters the Chlamydia cells in a manner which renders the antigen more available for adherence to the amidine modified latex and binding to the tracer may be used. Conventional techniques as described by Armstrong et al., supra or the patented procedure of Rose supra may be used. A preferred reagent for alteration of the Chlamydia cells contains a chelating agent, a protein and a surfactant in a buffer and is described in detail in one of the Examples.

Adherence of the Chlamydia antigen to the amidine latex particles may be carried out for any length of time preferably about 1 to 60 minutes at any suitable temperature, preferably about 10° to 40° C., sufficient to cause firm adherence. In general, adherence of the antigen takes place readily and is substantially complete after about 15 minutes at 37° C.

In accordance with the invention, a greatly improved assay is achieved by using an amidine modified latex. It is believed, although not yet substantiated, that a specific interaction occurs between the amidine groups on the latex particles and the Chlamydia antigen, as evidenced by the inferior results obtained in the absence of amidine groups.

The Chlamydia antigen adhered to the amidine modified latex may be contacted with a tracer for the antigen. The tracer preferably is an antibody specific for the antigen having a label which is conjugated to the antibody. The label may be a radioactive atom, a fluorescent dye or an enzyme capable of detection by a signal associated with the label. The most preferred tracer is an anti-Chlamydia monoclonal antibody having an enzyme conjugated thereto which has been raised by conventional fusion and selection techniques. Procedures for raising monoclonal antibodies and conjugating a radiolabel, dye or enzyme to an antibody are well-known and no further details are needed for a complete understanding of this aspect of the invention by one skilled in the art.

Any enzyme which may be conjugated to an antibody and which can convert a substrate to a colored product may serve as the label. A preferred enzyme is a peroxidase, such as horseradish peroxidase (HRP) or, most preferably, a hydrolase. A suitable hydrolase is, for example, a peptidase, esterase, such as carboxyesterase, a glycosidase, such as galactosidase or most preferably, a phosphatase such as alkaline phosphatase (AP).

Binding of the antibody component of the tracer to the antigen adhered to the latex is wholly conventional, and is generally complete in about 1 to 10 minutes at ambient temperature.

The latex particles having a bound fraction thereon are separated from the liquid by any convenient procedure. For example, the assay medium may be centrifuged, the pellet of particles separated by decanting the liquid and the pellet resuspended in a second liquid. In this embodiment of the invention, the substrate may be added to the second liquid, and the presence of Chlamydia in the body sample ascertained by the development of color in the second liquid. This embodiment of the invention is preferred when it is desired to quantitate the antigen. Thus, the magnitude of the color may be measured with an instrument such as a colorimeter or a spectrophotometer and compared with the magnitude of the color formed when the assay is repeated with liquids containing a known quantity of antigen. It is evident that this embodiment is also preferred if a dye or radiolabel is used, in which case the antigen is detected by fluorescence from the dye after application of excitation light or by a determination of radioactive counts.

In the preferred embodiment of the invention requiring only detection of the antigen, separation of the particles from the liquid may be performed by filtration using a membrane having a pore size suitable for retention of the particles on the membrane surface. Suitable membranes are, for example, nylon membranes such as Immunodyne ®, Pall Corp., Glen Cove, N.Y.; Immobilon ®, Millipore Corp., Bedford, Mass.; and nitrocellulose membranes available from MSI, Westboro, Mass., and from Millipore. Most preferably, the membrane is pretreated with an inert protein, such as casein or albumin, to fill binding sites on the membrane which otherwise would nonspecifically bind to unbound tracer in the liquid leading to color not due to bound antigen. If desired, the membrane filters may be provided in the form of wells, such as the wells of a conventional microtiter plate, and may further be provided with structure to aid in filtration, such as a connection to a vacuum source or a layer of absorbent material under the filter.

After filtration, the particles on the membrane surface are preferably washed, preferably with a detergent, such as sodium dodecyl sulfate (SDS) and finally with deionized water. The washed membrane may then be treated with substrate solution. Any substrate which reacts with the enzyme label to give a colored product may be used. Thus, if the enzyme is HRP, suitable substrates are diaminobenzidine or, preferably, ortho phenylenediamine. If the enzyme is an esterase, the substrate may be, for example, p-nitrophenyl acetate or butyrate. If the substrate is a phosphatase such as the preferred alkaline phosphatase, suitable substrates are phosphates, such as p-nitrophenyl phosphate or indoxyl phosphate. The substrate may be present in the substrate solution at a concentration of about 0.1 to 10 mM, preferably about 1 to 5 mM. Selection of a suitable substrate and the concentration thereof to be used is well within the purview of one skilled in the art.

It has been found that color intensity is magnified if the substrate solution additionally contains a small quantity of a color enhancer. A suitable color enhancer is, for example, a tetrazolium salt. Accordingly, the most preferred substrate solution contains about 0.01 to 0.1 mg/mL of nitroblue tetrazolium in methanol.

In general, the reaction of enzyme and substrate to form the colored product is rapid, and a time of about 1 to 15 minutes, preferably about 3 to 5 minutes, is sufficient for color formation. The color forming reaction may be allowed to go for any length of time before being judged positive (color, therefore antigen present) or negative (no color, therefor no antigen). Alternatively, the reaction may be stopped at any time after combining enzyme and substrate with a stop solution. The stop solution inhibits enzyme activity and thereby freezes color development at the point of addition of the stop solution. A suitable stop solution is, for example, 10 mM ethylenediamine tetraacetic acid in 0.2 M sodium phosphate.

As mentioned above, if the label is a fluorescent dye, such as fluorescein, antigen may be detected by subjecting the dye to excitation light and detecting fluorescence. If a radiolabel is used, antigen detection may be performed by determining radioactive counts.

Another aspect of the invention is a kit of materials for performing the method of the invention. The kit may contain a latex of amidine modified polystyrene particles, an anti-Chlamydia antibody conjugated to an enzyme, a substrate reactive with the enzyme, and a membrane having a pore size sufficient to remove the particles when the latex is passed through the membrane. The kit may also include a reagent for altering Chlamydia organisms, solutions, such as buffers and saline, one or more solutions containing a predetermined quantity of Chlamydia antigen, and various utensils, such as containers and droppers useful in performing the assay of the invention. The kit may be assembled in a housing, preferably plastic, containing a material positioned under the membrane, such as absorbent paper, to facilitate flow of assay liquids through the membrane.

The following Examples are provided to further illustrate the invention but are not intended in any way to be limitative of the invention.

EXAMPLE I

To a DispensTube ® (Becton Dickinson) was added 40 μL of an extraction reagent (5 mM ethylenediamine tetraacetic acid, 0.5% bovine serum albumin, 5% V/V polyoxyethylene p-t octyl phenol surfactant in 0.5% W/V chenodeoxycholate/phosphate buffered saline, pH 7.2) and 130 μL of a Chlamydia clinical sample in the above buffer. The final volume of 200 μL was vortexed, set aside at ambient temperature for 5 minutes, and 50 μL of 1% amidine polystyrene latex, 1.15 were added. The mixture was vortexed and incubated at 37° C. for 15 minutes.

A solution of 250 μL of monoclonal anti-Chlamydia AP conjugate diluted with 40% V/V fetal bovine serum and 0.5% W/V casein buffer containing 10 mM tris and 154 mM NaCl, pH7.6 was added to give a conjugate concentration of 1.5 ug/ml. After vortexing and incubating for 5 minutes, the mixture was pipetted onto a casein blocked 0.65 Immunodyne ® membrane separated from 3 layers of absorbent pads by a piece of Schleicher and Schnell #5-S rayon.

To the amidine-latex particles thus filtered onto the membrane surface were added 600 μL of 5 mM SDS, pH 7 followed by 300 μL of distilled water. After the water wash had filtered through, 150 μL of substrate solution (1.5 mM disodium indoxyl phosphate, 0.5 mM magnesium chloride and 0.01% W/V nitro blue tetrazolium) were added. Color was allowed to develop for 3 to 5 minutes, then stopped with a solution containing 0.2 M sodium phosphate and 10 mM ethylenediamine tetraacetic acid.

The presence of Chlamydia in the clinical sample was indicated by the dark color on the membrane. A negative control sample (no Chlamydia) was indicated by no color on the membrane.

EXAMPLE II

The procedure of Example I was repeated with a tissue grown Chlamydia sample and several latexes which did not contain amidine groups. The following results were obtained, the densitometric signals being given in arbitrary units of color density:

| Latex | Densitometric Signals (OD) |
| --- | --- |
| Carboxylated (1.02 μm, Polyscience, Warrington, Pennsylvania) | 0.47 |
| Sulfated (1.05μ, Interfacial Dynamics, Portland, Oregon) | 0.37 |
| Methyl Methacrylate (0.3–0.4μ) | 0.17 |
| Carboxy-modified (Seragen, Indianapolis, Indiana) | 0.27 |
| Amidine (Latex of Example I) | 2.18 |

It is seen that color density is up to ten times greater using the amidine modified latex. The assay of the invention using amidine modified latex is thus of higher sensitivity and can be expected to detect Chlamydia organisms in samples which may be diagnosed as negative when assayed without amidine modified latex.

Thus, the method includes adhering Chlamydia antigen to amidine modified latex particles. Use of the amidine modified latex provides an assay of enhanced sensitivity because the antigen adheres firmly to the amidine modified latex in greater quantity than occurs with other latexes which are not amidine modified.

What is claimed is:

1. A method for determining Chlamydia antigen comprising:
    a) contacting particles of an amidine modified latex with a liquid suspected of containing Chlamydia antigen whereby said antigen adheres to said particles;
    b) contacting said particles having antigen adhered thereto with an anti-Chlamydia antibody conjugated to an enzyme whereby said antigen on said particles binds to said antibody to give a bound fraction containing said enzyme on said particles;
    c) separating said particles on said bound fraction from said liquid;
    d) contacting the enzyme on said separated particles with a substrate reactive with said enzyme whereby said enzyme converts said substrate to a product; and
    e) detecting the presence of Chlamydia antigen in said sample by the appearance of color associated with said product.

2. The method of claim 1 further comprising determining the concentration of said Chlamydia antigen in said liquid by comparing the magnitude of said color with the magnitude of color established for a known quantity of the antigen.

3. The method of claim 1 wherein said latex is selected from the group consisting of polystyrene, styrene butadiene copolymer and polyacrylate.

4. The method of claim 1 wherein said enzyme is selected from the group consisting of a peroxidase and a hydrolase.

5. The method of claim 4 wherein said hydrolase is selected from the group consisting of alkaline phosphatase, galactosidase and carboxyesterase.

6. The method of claim 1 wherein said antibody is a monoclonal antibody.

7. The method of claim 1 wherein said separating is performed by centrifugation.

8. The method of claim 1 wherein said separating is performed by filtration through a membrane.

9. The method of claim 8 wherein said membrane is pretreated with an inert protein.

10. The method of claim 1 wherein the enzyme on the separated particles is additionally contacted with a tetrazolium salt.

11. The method of claim 10 wherein said salt is nitroblue tetrazolium.

12. A method for determining Chlamydia antigen comprising:
   a) adhering Chlamydia antigen in a liquid to an amidine derivatized solid support;
   b) contacting antigen adhered to said support with an antibody having a label conjugated thereto, said antigen binding to said antibody to give a bound fraction containing said label on said support;
   c) separating said support from said liquid; and
   d) detecting said antigen by a signal associated with said label.

13. The method of claim 12 wherein said label is selected from the group consisting of a radioactive atom, a fluorescent dye and an enzyme.

14. The method of claim 13 wherein said label is a radioactive atom and said detecting is performed by measuring radioactive counts from said bound fraction.

15. The method of claim 13 wherein said label is a fluorescent dye, and said detecting is performed by subjecting said bound fraction to excitation light and measuring fluorescence from said bound fraction.

16. A method for determining Chlamydia organisms in a liquid comprising:
   a) subjecting a liquid suspected of containing Chlamydia organisms to a reagent for exposing Chlamydia antigen;
   b) contacting said liquid with a latex containing amidine modified particles whereby said antigen adheres to said particles;
   c) contacting said particles having adhered antigen with a monoclonal antibody conjugated to alkaline phosphatase whereby said antigen adhered to said particles binds to said antibody to give a bound fraction containing alkaline phosphatase on said particles;
   d) filtering said latex through a membrane having a pore size sufficient to retain said particles;
   e) adding a substrate reactive with said alkaline phosphatase to said membrane; and
   f) detecting the presence of Chlamydia organisms in said liquid by the appearance of color on said membrane.

17. The method of claim 16 wherein said reagent contains a detergent.

18. A kit of materials for performing an assay for Chlamydia comprising a latex of amidine modified polystyrene particles, an anti Chlamydia antibody conjugated to an enzyme, a substrate reactive with said enzyme, and a membrane for filtering said particles.

19. The kit of claim 18 further comprising a reagent for altering Chlamydia organisms.

20. The kit of claim 18 further comprising one or more solutions containing a predetermined quantity of Chlamydia antigen.

21. The kit of claim 20 further comprising a solution or utensil useful in performing the assay of the invention.

22. The kit of claim 18 further comprising a housing for assembly of the components of said kit, said housing containing an absorbent material positioned under said membrane.

* * * * *